United States Patent
Mullen et al.

(10) Patent No.: US 12,115,083 B2
(45) Date of Patent: Oct. 15, 2024

(54) AUGMENTED, JUST-IN-TIME, PATIENT-SPECIFIC IMPLANT MANUFACTURE

(71) Applicant: Howmedica Osteonics Corp., Mahwah, NJ (US)

(72) Inventors: Lewis Mullen, Englewood, NJ (US); Robert Carter, Warwick, NY (US); Marc Esformes, Fishkill, NY (US); Chau Ngo, Secaucus, NJ (US); Richard Wood, Howell, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 812 days.

(21) Appl. No.: 16/713,282

(22) Filed: Dec. 13, 2019

(65) Prior Publication Data

US 2020/0188134 A1 Jun. 18, 2020

Related U.S. Application Data

(60) Provisional application No. 62/779,603, filed on Dec. 14, 2018.

(51) Int. Cl.
*A61F 2/46* (2006.01)
*A61F 2/30* (2006.01)
(Continued)

(52) U.S. Cl.
CPC .......... *A61F 2/46* (2013.01); *A61F 2/30734* (2013.01); *A61B 2034/108* (2016.02); *A61F 2002/2825* (2013.01); *A61F 2002/2892* (2013.01); *A61F 2002/30387* (2013.01); *A61F 2002/30616* (2013.01); *A61F 2002/30736* (2013.01); *A61F 2002/30952* (2013.01); *A61F 2002/30985* (2013.01); *A61F 2/32* (2013.01); *A61F 2/40* (2013.01); *A61F 2/4225* (2013.01);
(Continued)

(58) Field of Classification Search
CPC .......... A61F 2002/30736; A61F 2/4637; A61F 2002/30952; A61F 2002/30985; A61F 2002/4633; A61F 2002/4632; A61B 34/30; A61B 34/32; A61B 34/10; A61B 2034/108; A61B 2034/104
See application file for complete search history.

(56) References Cited

U.S. PATENT DOCUMENTS 4,936,847 A * 6/1990 Manginelli ........... A61F 2/3859
623/20.16
4,944,757 A * 7/1990 Martinez ................ A61F 2/389
623/20.15

(Continued)

FOREIGN PATENT DOCUMENTS

WO 2018136393 A1 7/2018

OTHER PUBLICATIONS

Extended European Search Report for Application No. EP19216169.3, dated Apr. 14, 2020, pp. 1-4.

*Primary Examiner* — Alvin J Stewart
(74) *Attorney, Agent, or Firm* — Lerner David LLP (57) ABSTRACT

A bone part is repaired by a process. A first implant is attached to a first bone part. The first implant corresponds to an intraoperatively defined or an intraoperatively selected cutting path. A preoperatively defined second implant is attached to the first implant. The first implant and the second implant together augment the first bone part.

19 Claims, 6 Drawing Sheets

(51) Int. Cl.
 A61B 34/10 (2016.01)
 A61F 2/28 (2006.01)
 A61F 2/32 (2006.01)
 A61F 2/40 (2006.01)
 A61F 2/42 (2006.01)
 A61F 2/44 (2006.01)
 B33Y 80/00 (2015.01)

(52) U.S. Cl.
 CPC .............. *A61F 2/4261* (2013.01); *A61F 2/44* (2013.01); *A61F 2002/4633* (2013.01); *A61F 2/4637* (2013.01); *B33Y 80/00* (2014.12)

(56) References Cited

U.S. PATENT DOCUMENTS

| | | | | |
|---|---|---|---|---|
| 5,047,058 A | * | 9/1991 | Roberts | A61F 2/30734 623/20.16 |
| 5,080,674 A | * | 1/1992 | Jacobs | A61F 2/38 623/20.17 |
| 5,152,797 A | * | 10/1992 | Luckman | A61F 2/30771 623/20.16 |
| 5,176,711 A | * | 1/1993 | Grimes | A61F 2/4684 623/22.22 |
| 5,192,329 A | * | 3/1993 | Christie | A61F 2/4609 623/22.22 |
| 5,326,368 A | * | 7/1994 | Collazo | A61F 2/30734 623/22.22 |
| 5,344,461 A | * | 9/1994 | Phlipot | A61F 2/4684 623/20.16 |
| 5,370,693 A | * | 12/1994 | Kelman | A61F 2/30724 623/16.11 |
| 6,299,645 B1 | | 10/2001 | Ogden | |
| 7,537,664 B2 | | 5/2009 | O'Neill et al. | |
| 8,652,148 B2 | | 2/2014 | Zuhars | |
| 8,728,387 B2 | | 5/2014 | Jones et al. | |
| 9,180,010 B2 | | 11/2015 | Dong et al. | |
| 9,358,114 B2 | | 6/2016 | Hughes | |
| 9,456,901 B2 | | 10/2016 | Jones et al. | |
| 9,913,704 B1 | * | 3/2018 | Yaremchuk | A61F 2/02 |
| 10,433,921 B2 | | 8/2019 | Librot | |
| 11,013,606 B2 | | 5/2021 | Masini et al. | |
| 2007/0234819 A1 | * | 10/2007 | Amirouche | G01L 1/2225 73/781 |
| 2008/0319491 A1 | * | 12/2008 | Schoenefeld | A61B 17/1703 606/86 R |
| 2011/0190899 A1 | * | 8/2011 | Pierce | A61F 2/389 623/18.11 |
| 2011/0306978 A1 | | 12/2011 | Ries et al. | |
| 2013/0035766 A1 | * | 2/2013 | Meridew | A61F 2/34 623/22.21 |
| 2013/0211792 A1 | * | 8/2013 | Kang | A61B 34/30 703/1 |
| 2014/0257499 A1 | * | 9/2014 | Winslow | A61F 2/4081 623/19.13 |
| 2014/0371897 A1 | | 12/2014 | Lin et al. | |
| 2015/0112443 A1 | * | 4/2015 | Gelaude | A61F 2/30 700/98 |
| 2015/0343708 A1 | | 12/2015 | Gerstle et al. | |
| 2016/0193051 A1 | * | 7/2016 | Budhabhatti | A61F 2/32 623/22.21 |
| 2016/0310285 A1 | * | 10/2016 | Kovacs | A61B 17/1778 |
| 2016/0317307 A1 | | 11/2016 | Bailey et al. | |
| 2016/0317312 A1 | * | 11/2016 | Bojarski | A61B 17/157 |
| 2017/0165790 A1 | | 6/2017 | McCarthy et al. | |
| 2017/0181755 A1 | | 6/2017 | Librot | |
| 2017/0312032 A1 | * | 11/2017 | Amanatullah | G09B 23/30 |
| 2018/0008418 A1 | | 1/2018 | Bonutti | |
| 2018/0014891 A1 | * | 1/2018 | Krebs | A61B 5/055 |
| 2018/0049878 A1 | * | 2/2018 | Stulberg | A61F 2/389 |
| 2018/0140427 A1 | | 5/2018 | Conway et al. | |
| 2018/0193152 A1 | * | 7/2018 | Bauer | A61F 2/447 |
| 2018/0233222 A1 | * | 8/2018 | Daley | G16H 50/50 |
| 2018/0333207 A1 | * | 11/2018 | Moctezuma De la Barrera | A61B 34/10 |
| 2018/0344465 A1 | * | 12/2018 | McPherson | A61F 2/30771 |
| 2019/0000629 A1 | * | 1/2019 | Winslow | A61F 2/4612 |
| 2019/0076198 A1 | * | 3/2019 | Berend | A61B 17/1721 |
| 2019/0142520 A1 | * | 5/2019 | VanDyken | G09B 23/30 606/1 |
| 2019/0272917 A1 | * | 9/2019 | Couture | G16H 40/67 |
| 2019/0290361 A1 | * | 9/2019 | Shalayev | A61B 34/10 |
| 2019/0365346 A1 | * | 12/2019 | Elliot | A61B 8/0875 |
| 2019/0388158 A1 | * | 12/2019 | Mahfouz | A61B 17/1764 |
| 2020/0268448 A1 | * | 8/2020 | Weir | G06N 3/08 |
| 2020/0297357 A1 | * | 9/2020 | Cameron | A61B 17/162 |
| 2021/0015560 A1 | * | 1/2021 | Boddington | G16H 50/70 |
| 2021/0378829 A1 | * | 12/2021 | Dmuschewsky | A61F 2/3859 |
| 2022/0000627 A1 | * | 1/2022 | Brazil | A61F 2/389 |
| 2022/0047329 A1 | * | 2/2022 | Lavallee | A61B 34/25 |
| 2022/0175453 A1 | * | 6/2022 | Xu | A61B 34/10 |
| 2022/0211507 A1 | * | 7/2022 | Simoes | A61B 5/1077 |
| 2022/0273450 A1 | * | 9/2022 | Steines | A61F 2/30942 |
| 2022/0338935 A1 | * | 10/2022 | Bell | A61B 17/1626 |
| 2023/0023117 A1 | * | 1/2023 | Nikou | A61B 5/0053 |
| 2023/0080229 A1 | * | 3/2023 | Metcalfe | A61B 34/25 703/6 |

\* cited by examiner

AUGMENTED, JUST-IN-TIME, PATIENT-SPECIFIC IMPLANT MANUFACTURE

CROSS-REFERENCE TO RELATED APPLICATION

The present application claims the benefit of the filing date of U.S. Provisional Patent Application No. 62/779,603, filed Dec. 14, 2018, the disclosure of which is hereby incorporated herein by reference.

FIELD OF THE TECHNOLOGY

The present technology relates to systems and processes for the repair of bone defects, and in particular to the preparation of patient-specific implants intraoperatively.

BACKGROUND OF THE TECHNOLOGY

Patient-specific implants are medical devices generally intended to address indications in patients where reliance on standard sizes are not preferred. These indications may be the result of sufficiently rare conditions, the desire to preserve as much bone as possible, or other clinical issues. Such implants may be manufactured by modifying currently available implants or by fabricating completely unique implants to address the condition. In the case of surgeries to address oncological, revision, and trauma indications, massive bone loss and bone resorption can occur within a relatively short period of time making it difficult to approximate a patient's bone structure on the day of surgery. However, due to their design based on patient imaging, patient-specific implants need to be prepared prior to a scheduled surgery. Accordingly, in order to more closely match the patient-specific implant to the bone expected to be preserved, surgeons prefer to use computerized tomography (CT) or magnetic resonance imaging (MRI) imaging, for example, to define accurate margins very close to the date of surgery. However, both patients' and surgeons' schedules do not always allow for preoperative planning based on obtained images and models to be conducted close to the date of surgery, and indeed surgeries are sometimes postponed to a later date. Additionally, even when preoperative planning is conducted close to the date of surgery, surgeons may decide to alter their preoperatively planned cutting paths during the surgery.

Accordingly, there is a need to provide additional tools and procedures to allow for intraoperative modifications to patient-specific implants.

SUMMARY OF THE TECHNOLOGY

In accordance with an aspect, a patient-specific first implant may be fabricated preoperatively. A bone part may be resected according to a preoperative plan to form a remaining bone part. A patient-specific second implant may be fabricated intraoperatively. The second implant may be attached to the remaining bone part, and the first implant may be attached to the second implant. In this manner, a combination of the bone part, the first implant, and the second implant may have a predetermined structure defined preoperatively.

In some arrangements, the first implant may be a hip implant, a shoulder implant, a femoral implant, a tibial implant, a spine implant, a wrist implant, or a foot implant. In some arrangements, the second implant may be in the form of a shim or a plurality of stacked and separable shims. In some such arrangements with a plurality of shims, the plurality of shims may be attached in a tongue-and-groove configuration to form a joint.

In accordance with another aspect, a patient-specific first implant may be fabricated preoperatively, and a plurality of differently sized implants may be fabricated preoperatively. A bone part may be resected according to a preoperatively planned first cutting path. The bone part then may be resected according to a preoperatively planned second cutting path corresponding to a selected one of the plurality of differently sized implants. The selected one of the plurality of differently sized implants may be attached to the bone part, and the first implant may be attached to the selected one of the plurality of differently sized implants. In this manner, a combination of the bone part, the first implant, and the selected one of the plurality of differently sized implants may have a predetermined structure defined preoperatively.

In some arrangements, the selected one of the plurality of differently sized implants may be in the form of a shim or a plurality of stacked and separable shims. In some such arrangements with a plurality of shims, the plurality of shims may be attached in a tongue-and-groove configuration to form a joint.

In some arrangements, the first implant may be a hip implant, a shoulder implant, a femoral implant, a tibial implant, a spine implant, a wrist implant, or a foot implant. In some such arrangements, the differently sized implants may be shims.

In accordance with another aspect, a tissue defect, which may be a bone part, may be repaired by a process. In this process, a first implant may be attached to a first bone part. The first implant may correspond to an intraoperatively defined or intraoperatively selected cutting path. A preoperatively defined second implant may be attached to the first implant. The first implant and the second implant together augment the first bone part.

In some arrangements, the first bone part may be an existing bone part. In some such arrangements, the first bone part may be an entire bone.

In some arrangements, the first bone part may include a resected bone surface to which the first implant is attached.

In some arrangements, the first implant may be selected from a kit of differently dimensioned implants.

In some arrangements, the second implant may be attached to a second bone part to form a joint defined by the first implant, the second implant, the first bone part, and the second bone part. In some such arrangements, the second bone part may be an entire bone.

In some arrangements, an initial bone part may be resected to form the first bone part.

In some arrangements, the second implant may be a hip implant, a shoulder implant, a femoral implant, a tibial implant, a spine implant, a wrist implant, or a foot implant. In some such arrangements, the first implant may be a shim.

In some arrangements, the second implant may be configured to replace a mid-section of an initial bone part resected to form the first bone part.

In some arrangements, the second implant may be a shim.

In some arrangements, either one or both of the first implant and the second implant may be fabricated intraoperatively. In some such arrangements, the respective one or both of the first implant and the second implant may be fabricated by three-dimensional (3D) printing. In some such arrangements, a computer-aided design (CAD) model of the respective one or both of the first implant and the second implant may be generated intraoperatively for use in the fabrication by 3D printing. In some such arrangements, an initial bone part may be resected to form the first bone part and to define a resected bone section. In such arrangements, a Boolean operation between a CAD model of the resected bone section and a CAD model of the second implant may be performed during the process of generating the CAD model of the first implant.

In some arrangements, the first implant may be 3D printed onto the second implant such that the first implant is fused to the second implant. In some arrangements, the first implant may be attached to the second implant by one or more fasteners. In some such arrangements, any one of the one or more fasteners may be a screw.

In some arrangements, the fabrication of the respective one or both of the first implant and the second implant may include either one or both of computer numerically controlled (CNC) milling or CNC lathing of a block of material.

In some arrangements, either one or both of the first implant and the second implant may have a lattice structure, unit cell structure, a woven structure, or a chain mail structure. In some arrangements, either one or both of the first implant and the second implant may be solid. In some arrangements, either one or both of the first implant and the second implant may be partially or wholly made of any one or any combination of metal, plastic, and ceramic. In some arrangements, either one or both of the first implant and the second implant may be bio-resorbable. In some arrangements, either one or both of the first implant and the second implant may be non-resorbable and biocompatible. In some arrangements, either one or both of the first implant and the second implant may be partially or wholly made of either one or both of autograft or allograft material.

In some arrangements, an initial bone part may be resected to form an intermediate bone part according to a preoperatively defined cutting path and to define a first resected bone section. In such arrangements, the intermediate bone part may be resected according to the intraoperatively selected cutting path to form the first bone part and to define a second resected bone section. The intraoperatively selected cutting path may be selected among a plurality of preset cutting paths different from the preoperatively defined cutting path. The second resected bone section may correspond to the first implant.

In some arrangements, the first implant may be dimensioned the same as a volume defined by the second resected bone section. In some arrangements, a CAD model of the second resected bone section may have the same dimensions as a CAD model of the first implant.

In some arrangements, the augmented bone part may have a predetermined structure corresponding to a CAD model. In some arrangements, the CAD model may be prepared preoperatively, while in other arrangements, the CAD model may be prepared intraoperatively.

In some arrangements, the second implant may be a patient-specific implant.

In some arrangements, the second implant may be a hip implant, a shoulder implant, a femoral implant, a tibial implant, a spine implant, a wrist implant, or a foot implant. In some arrangements, the second implant may be in the form of a shim or a plurality of stacked and separable shims. In some such arrangements with a plurality of shims, the plurality of shims may be attached in a tongue-and-groove configuration to form a joint.

In accordance with another aspect, an implant system for repairing a bone part may include a first implant and a preoperatively defined second implant. The first implant may be shaped substantially the same as a first removed portion of bone removed from a bone part prior to removal of the first removed portion from the bone part. The first implant may be configured for attachment to a remaining portion of the bone part after the removal of the first removed portion. The second implant may be shaped substantially the same as a second removed portion of bone removed from the bone part prior to removal of the second removed portion from the bone part. The second removed portion of bone may be directly adjacent to the first removed portion of bone prior to the removal of the first and the second removed portions of bone from the bone part. The second implant may be configured for attachment to the first implant. The first implant and the second implant together may augment the bone part such that the augmented bone part has a predefined structure defined prior to fabrication of either one or both of the first implant and the second implant.

In accordance with another aspect, an implant system for repairing a bone part may include a first implant and a preoperatively defined second implant. The first implant may be configured for replacing a first removed portion of bone removed from a bone part. The first implant may be configured for attachment to a remaining portion of the bone part after the removal of the first removed portion. The second implant may be configured for replacing a second removed portion of bone removed from the bone part. The second removed portion of bone may be directly adjacent to the first removed portion of bone prior to the removal of the first and the second removed portions of bone from the bone part. The second implant may be configured for attachment to the first implant. The first implant and the second implant together may augment the bone part such that the augmented bone part has a predefined structure defined prior to fabrication of either one or both of the first implant and the second implant.

In some arrangements, the first implant may correspond to a first preset cutting path, and the second implant may correspond to a preoperatively defined cutting path. In some arrangements, the first preset cutting path may be intraoperatively defined. In some arrangements, the preoperatively defined cutting path may be a second preset cutting path. In some arrangements, the first preset cutting path may be a cutting path selected among a plurality of preset cutting paths different from the second preset cutting path.

In some arrangements, either one or both of the first implant and the second implant may be in the form of a shim or a plurality of stacked and separable shims. In some such arrangements, only the first implant may be in the form of a shim. In some arrangements with a plurality of shims, the plurality of shims may be attached in a tongue-and-groove configuration to form a joint.

In some arrangements, either one or both of the first implant and the second implant may have a maximum thickness less than or equal to 50 mm. In some such arrangements, only the first implant may have such a maximum thickness.

In some arrangements, either one or both of the first implant and the second implant may be a patient-specific implant. In some arrangements, the augmented bone part may have an intraoperatively defined patient-specific structure. In some other arrangements, the first implant may be selected intraoperatively from a kit of preoperatively defined implants such that the augmented bone part has a preoperatively defined structure.

BRIEF DESCRIPTION OF THE DRAWINGS

A more complete appreciation of the subject matter of the present technology and the various advantages thereof may be realized by reference to the following detailed description which refers to the accompanying drawings, in which.

DETAILED DESCRIPTION

As used herein, the term "preoperative" and similar terms refer to a period prior to detectable natural anatomical changes, e.g., bone loss, occurring in a bone part to be repaired, and the term "intraoperative" and similar terms refer to a period after the preoperative period, at which detectable natural anatomical changes do not occur in the bone part, and up to the time that a surgical operation concludes. As some examples, the intraoperative period may include the entire day of a surgical operation on the bone part, a week prior to the surgical operation, a month prior to the surgical operation, or other time periods during which detectable natural anatomical changes do not occur on the bone part.

Figure 1:
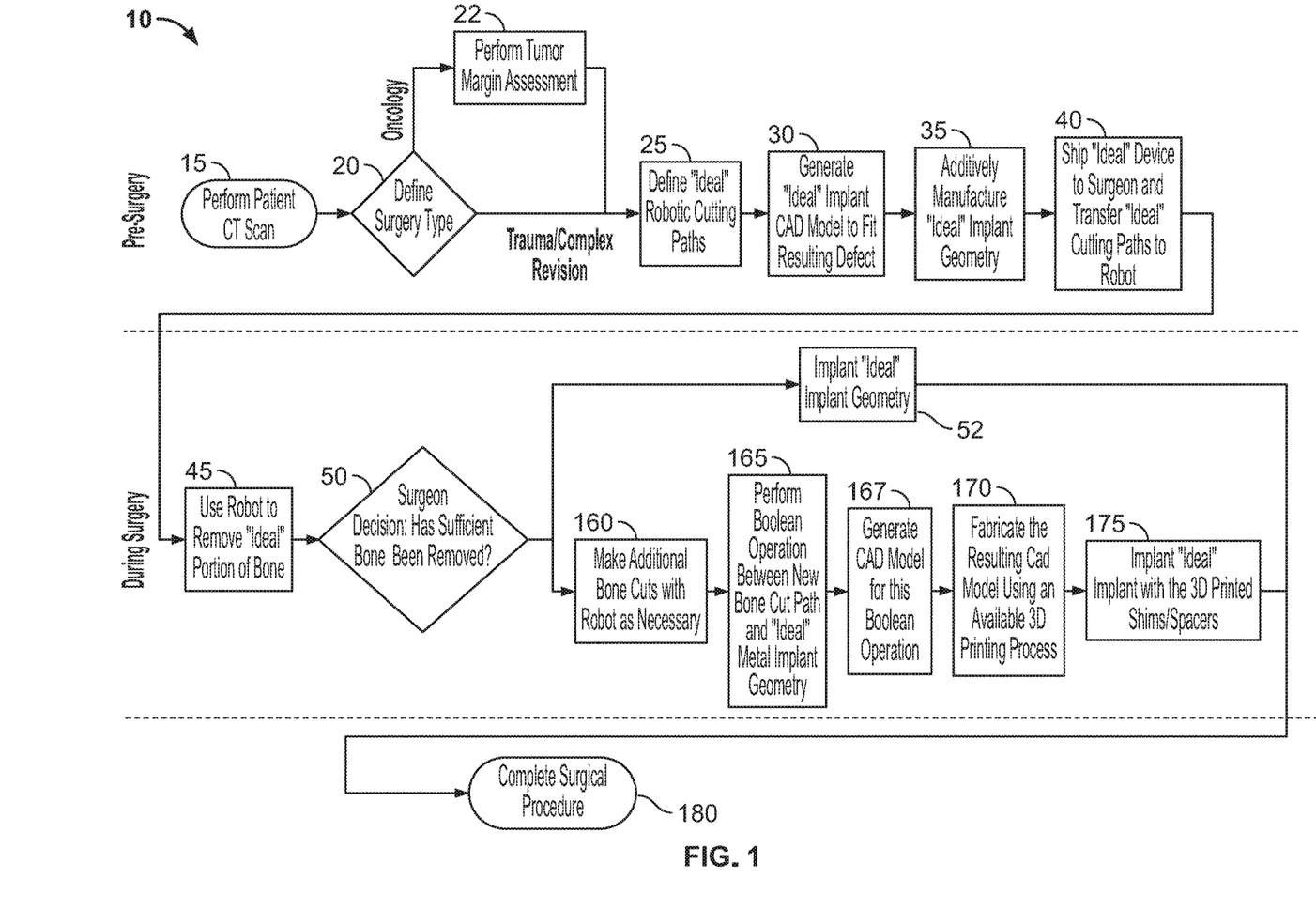
FIG. 1 is a process flow diagram of a process for repairing a bone defect in accordance with an embodiment.

Referring now to FIG. 1, bone repair process 10 may be a process for identifying a patient's need for a patient-specific prosthesis, for determining such prosthesis believed to be needed, for modeling and preparing such prosthesis, and for surgically implanting the prosthesis and in some instances, at least one additional prosthesis. In particular, at step 15 of process 10, a computer tomography (CT) scan of a patient is performed at the location of a presumed bone defect. Other scanning methods such as magnetic resonance imaging (MRI) or positron emission tomography (PET), for example, may be used to scan the patient. Upon evaluation of the scan, at step 20, a surgeon or other certified medical professional (hereinafter "surgeon") determines whether the defect is caused by a cancerous lesion and thus requires an oncological approach to treatment or is caused by a traumatic injury or other injury requiring a complex revision approach. When an oncological approach is determined to be needed, at step 22, a tumor margin assessment is made to ascertain an envelope of healthy tissue to be removed beyond the located tumor site for testing of any residual cancerous tissue. Next, at step 25, under either of the oncological and trauma/complex revision approaches, an "ideal" cutting path is defined, such as through analysis and manipulation of a virtual model of the bone defect site using computer-aided design (CAD) software tools known to those skilled in the art. The ideal cutting path may be defined for use by a robot during a robotic surgery. At step 30, a CAD model of an "ideal" implant is prepared based on and to fit with the virtual model of remaining bone after removal of the predetermined bone structure to be removed at step 25. At step 35, a physical implant corresponding to the modeled ideal implant is preferably fabricated preferably by an additive manufacturing process, such as but not limited to selective laser sintering (SLS), selective laser melting (SLM), electron beam melting (EBM), or other three-dimensional printing (3DP) processes known to those skilled in the art, although such implant may be fabricated using other manufacturing processes known to those skilled in the art such as but not limited to computer-aided manufacturing (CAM) and other subtractive fabrication processes. As complete implants, especially metallic ones, require significant production time, the implant is fabricated at a facility remote from the location of the eventual surgical operation. Accordingly, at step 40, the fabricated implant is shipped to the surgical location and a digital file containing instructional data corresponding to the predefined robotic cutting path is sent electronically to the surgical location and uploaded to a server or other digital storage media for use by the robot during robotic surgery.

Figure 2:
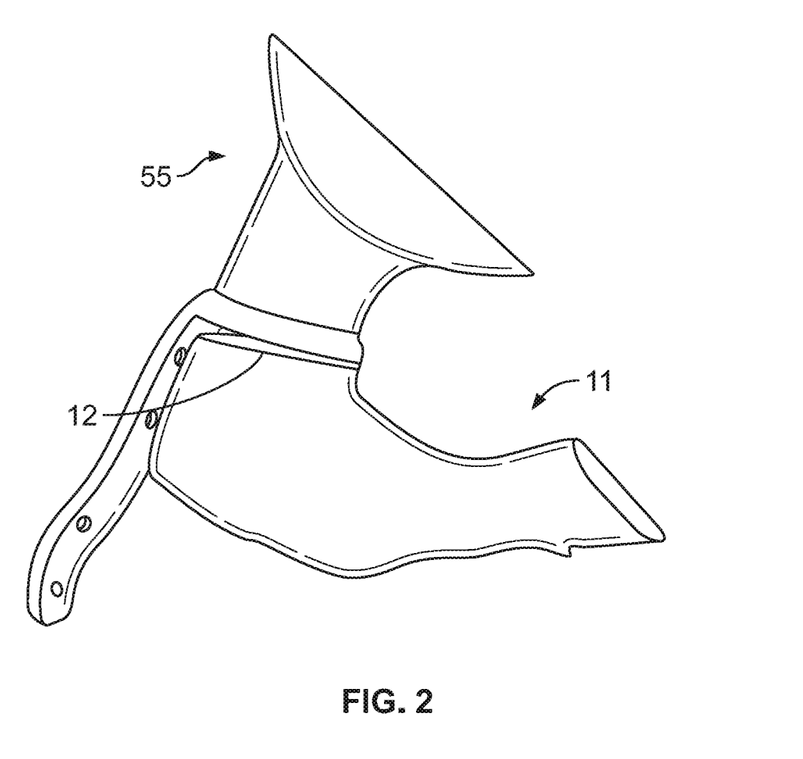
FIG. 2 is a perspective view of a patient-specific implant adjacent to a bone in accordance with an embodiment.

At step 45, preferably based on identified fiducial markers at the bone defect site, bone structure is removed at the defect site by the robot according to the predefined robotic cutting path. At step 50, the surgeon determines whether sufficient bone has been removed at the defect site. As demonstrated in FIG. 2, when the surgeon determines sufficient bone has been removed, at step 52, fabricated implant 55, which in this example and solely by way of example is a shoulder prosthesis, may be attached to prepared bone 11 at preoperative margin 12 of resection of the prepared bone formed by the removal of bone structure using the predefined robotic cutting path. In some alternative arrangements, data corresponding to a shape and volume of the removed bone structure may be tracked with a computer system operatively coupled to the surgical tool used to remove the bone, and implant 55 may be fabricated intraoperatively based on the tracked data, as described more fully in U.S. Pat. No. 10,433,921 B2 (hereinafter "the '921 Patent"), the disclosure of which is hereby incorporated by reference herein in its entirety.

Referring again to FIG. 1, if the surgeon determines that insufficient bone has been removed, at step 160, the surgeon may intraoperatively remove additional bone structure from prepared bone 11. Such bone may be removed through manual control of the robot by the surgeon in which case the path taken by the robot may be recorded into an augmented cutting path data file or by automatic removal by the robot based on an augmented cutting path data file that may be intraoperatively prepared within a virtual model using CAD software tools. Still referring to FIG. 1, at step 165, a Boolean operation is performed based on augmented cutting path data stored in the augmented cutting path data file prepared at step 160 and data corresponding to the CAD model of the "ideal" implant to create a new data file from which, at step 167, a CAD model for a spacer, which may be in the form of a shim like that of shim 195, may be generated. At step 170, a physical spacer may be fabricated intraoperatively using the CAD model generated at step 162. The physical spacer may be fabricated on the premises of the surgery. The spacer may be fabricated by additive manufacturing or subtractive manufacturing, and in some arrangements, may be fabricated within the operating room or near the operating room such as in an adjacent room to the operating room. In this manner, the physical spacer may be utilized promptly while the bone repair site is exposed. In some arrangements, the spacer may be made of any one or any combination of a bio-resorbable polymer, a non-resorbable, biocompatible polymer, a bio-resorbable metal, a non-resorbable, biocompatible metal, a bio-resorbable, biocompatible 3D printed metal, 3D printable artificial bone material, 3D printable autograft bone material, and 3D printable allograft bone material. In any arrangements made with a bio-resorbable polymer, such materials may be filled with bioactive agents such as but not limited to bioglass. The spacer may be made of any one or any combination of titanium, a titanium alloy, stainless steel, magnesium, a magnesium alloy, cobalt, a cobalt alloy, a cobalt chrome alloy, nickel, a nickel alloy, tantalum, and niobium, polyethylene (PE) and variations thereof, polyetheretherketone (PEEK), polyetherketone (PEK), acrylonitrile butadiene styrene (ABS), silicone, and cross-linked polymers, bioabsorbable glass, ceramics, and biological active materials including collagen/cell matrices.

When physical spacer 195 is fabricated by additive manufacturing, any available metal or polymer-based 3DP process may be employed. The additive manufacturing machine used for fabricating the spacer may be one for making either one or both of polymeric components and metallic components. To fabricate polymeric components, various processes including but not limited to stereolithograpy (SLA), digital light processing (DLP), fused deposition modeling (FUM), continuous liquid interface production (CLIP), SLS, and binder jetting may be employed. Machines for fabricating polymeric components may include, but are not limited to, the Formlabs® Form 2® SLA 3D Printer, the Makerbot® Replicator® 2X FDM 3D Printer, M1 printer by Carbon, Inc., and the FIG. 4 printer by 3D Systems, Inc. To fabricate metallic components, various processes including but not limited to SLS, SLM, and EBM may be employed. Machines for fabricating metallic components may include but are not limited to the Trumpf TruPrint 1000, the EOS® M 290, and the Arcam® EBM Q10plus. The spacer may be made of any one or any combination of a solid, porous, or other functionally stable structure. Any porous portions of the spacer may be in the form of lattice, mesh, or chain mail structures or structures having porous geometries in the form of unit cells such as portions of structures described in the combination of U.S. Pat. Nos. 7,537,664; 9,456,901 B2; 8,728,387 B2; 9,180,010 B2; and U.S. Patent Application Publication No. 2017/0165790 A1, the disclosures of each of which are hereby incorporated by reference herein in their entireties.

When spacer 195 is fabricated using subtractive manufacturing processes, one such process may be the use of computer-aided manufacturing (CAM) in which a computer numerically controlled (CNC) mill, lathe or other CNC machine is used to remove material from a block of metallic or polymeric material, as known to those skilled in the art.

Figure 3:
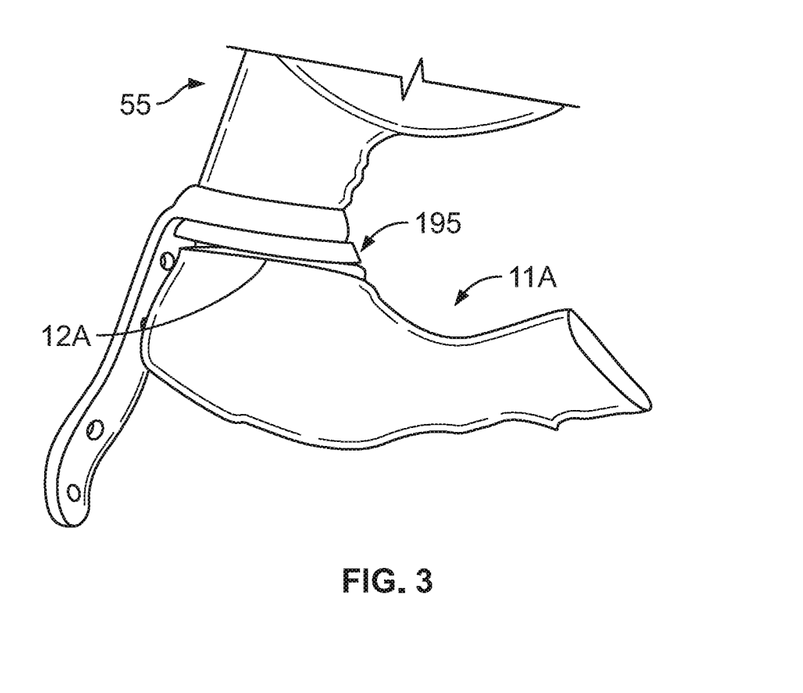
FIG. 3 is a perspective view of a patient-specific implant attached to a spacer adjacent to a bone in accordance with an embodiment.
Figure 4:
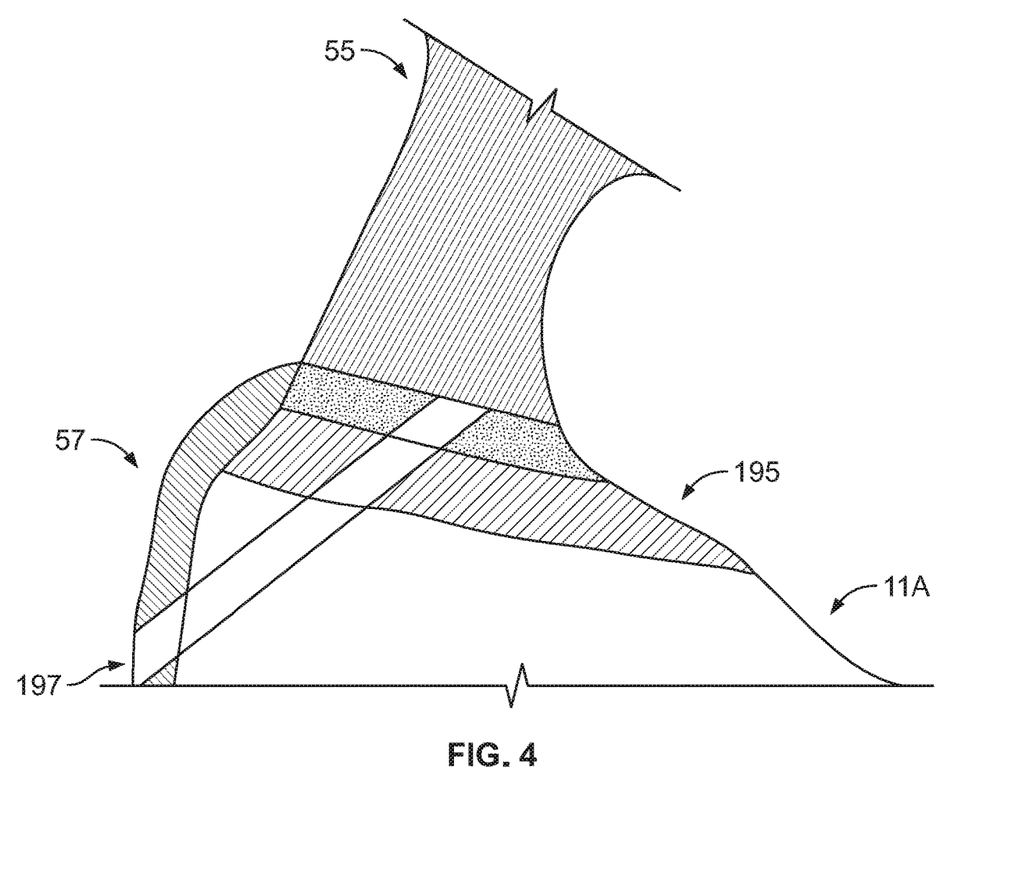
FIG. 4 is a cross-sectional view of a patient-specific implant adjacent to a spacer adjacent to a bone in accordance with an embodiment.

As demonstrated in FIG. 3, at step 175, fabricated spacer 195 may be attached to revised bone 11A at intraoperative margin 12A of resection of the revised bone formed by the removal of bone structure using the augmented cutting path data file and fabricated implant 55 may be attached to the spacer. In some arrangements, spacer 195 may be attached to implant 55, such as but not limited to by a fastener through both the spacer and the implant or by a later of bone cement between the spacer and the implant, prior to attaching the spacer, in combination with the implant, to revised bone 11A. In some other arrangements, spacer 195 may be attached to revised bone 11A prior to attaching implant 55 to the spacer which has been attached to the revised bone. As shown in FIG. 4, in still other arrangements, spacer 195 may be positioned against revised bone 11A, and then implant 55 may be placed against the spacer 195 and a fastener, such as a screw, may be inserted through hole 197 defined by each of the bone, the spacer, flange 57 and the implant to secure the bone, the spacer, and the implant together. In still further arrangements, implant 55 may act as a base onto which spacer 195 may be fabricated and to which the spacer may be fused using an additive manufacturing process.

Referring again to FIG. 1, after implant 55 is properly implanted, at step 180, the surgical procedure is completed. Completing the surgical procedure may include closing the repaired bone site and sterilizing instrumentation and equipment used during the surgical operation.

Figure 5:
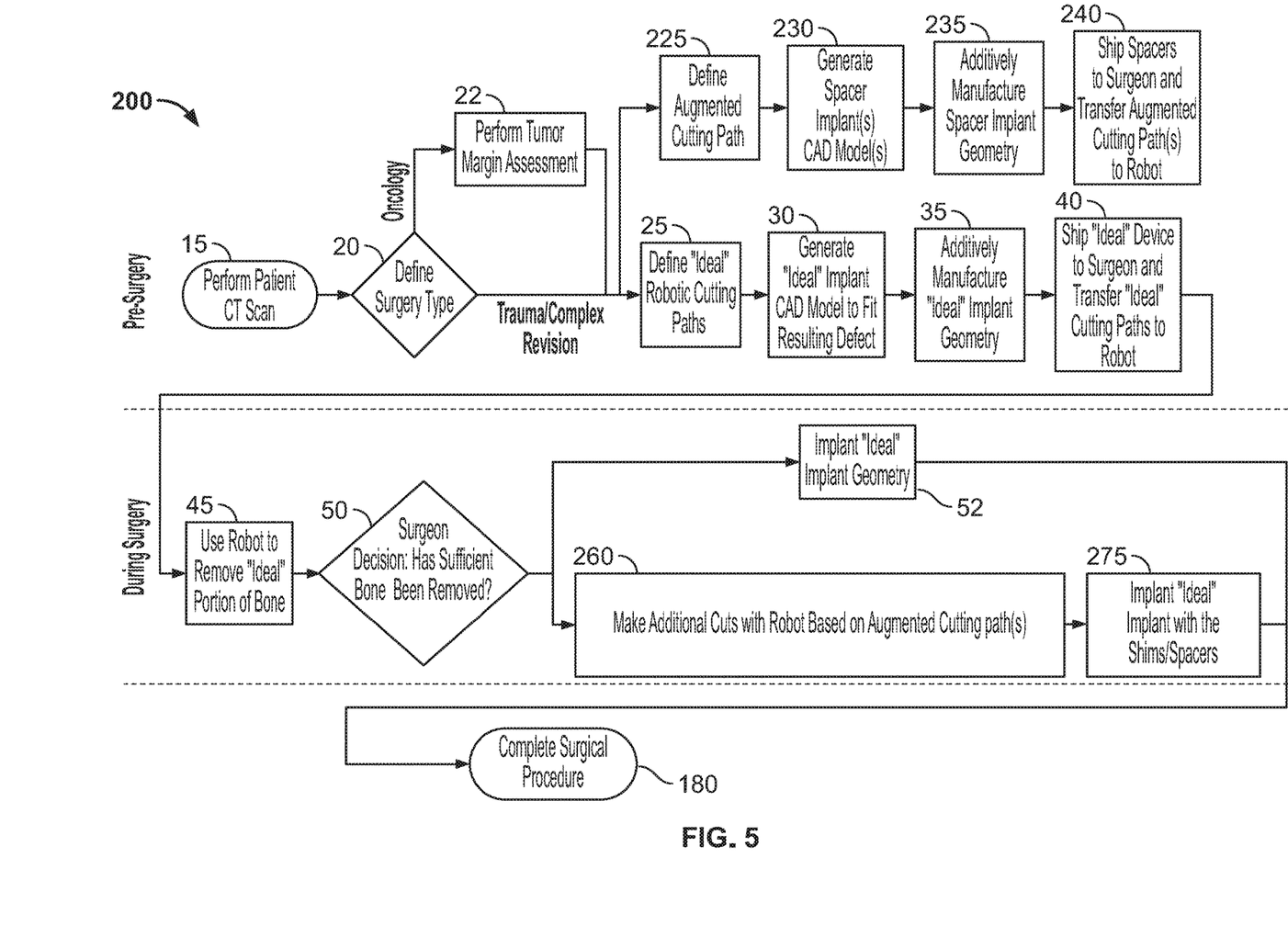
FIG. 5 is a process flow diagram of a process for repairing a bone defect in accordance with an embodiment.

Referring now to FIG. 5, bone repair process 200, like process 10, may be a process for identifying a patient's need for a patient-specific prosthesis, for determining such prosthesis believed to be needed, for modeling and preparing such prosthesis, and for surgically implanting the prosthesis and in some instances in the case or process 200, at least one additional prosthesis. Bone repair process 200 is the same as process 10 with the exception that process 200 includes steps 225, 230, 235, and 240 that may be taken in parallel or in series with steps 25, 30, 35, and 40 of process 10, and process 200 replaces steps 160, 165, 167, 170, or 175 of process 10 with steps 260 and 275. At step 225, under either of the oncological and trauma/complex revision approaches, one or more possible augmented cutting paths for use by the robot are defined and generated, such as through analysis and manipulation of a virtual model of the bone defect site using CAD software tools. In some arrangements, the augmented cutting paths may be based on existing patient population data, e.g., data found in the Stryker Orthopaedic Modeling and Analytics (SOMA) database.

At step 230, one or more CAD models of spacers of different dimensions, which may be of at least different thicknesses, are prepared based on and to fit with respective virtual models of remaining bone after removal of the predetermined bone structure to be removed by the respective augmented cutting paths at step 225. At step 235, one or more physical spacers corresponding to the modeled spacers are fabricated preferably by an additive manufacturing process, such as those described previously herein, although such spacers may be fabricated using other manufacturing processes known to those skilled in the art such as but not limited to CAM and other subtractive fabrication processes. Accordingly, at step 240, the fabricated spacers are shipped to the surgical location and digital files containing instructional data corresponding to each of the predefined augmented cutting paths are sent electronically to the surgical location and uploaded to a server or other digital storage media for use by the robot during robotic surgery.

At step 260, the surgeon may intraoperatively remove additional bone structure from prepared bone 11 based on one of the augmented cutting paths corresponding to one of the preoperatively fabricated spacers. At step 275, and again with reference to FIG. 3, one of the preoperatively fabricated spacers may be attached to revised bone 11A at intraoperative margin 12A of resection of the revised bone formed by the removal of bone structure using the chosen augmented cutting path data file and fabricated implant 55 may be attached to the preoperatively fabricated spacer.

Figure 6:
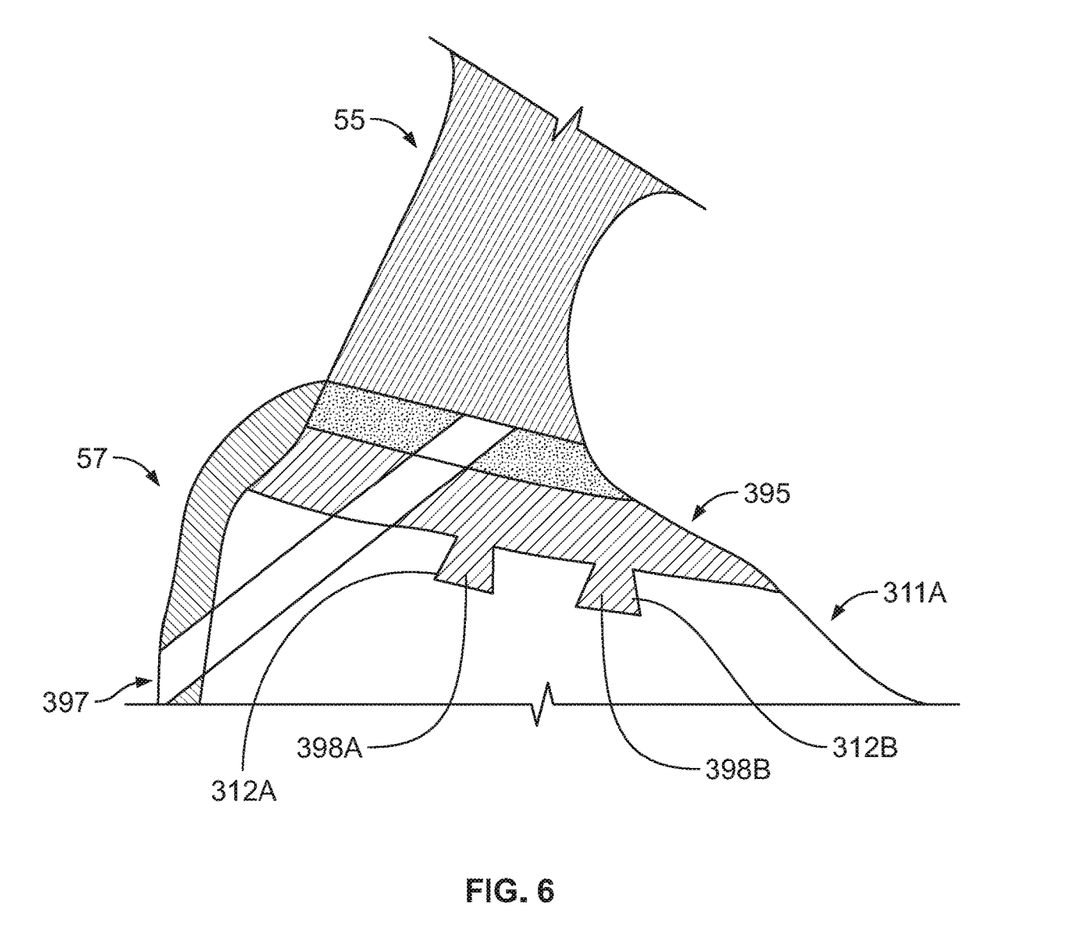
FIG. 6 is a cross-sectional view of a patient-specific implant adjacent to a spacer attached to a bone in accordance with an embodiment.

Referring now to the example of FIG. 6 in conjunction with processes 10, 200 of FIGS. 1 and 5, respectively, in some arrangements, at step 160 of process 10 or step 260 of process 200, the preparation of bone cuts includes preparing one or more keyways 312A, 312B defining portions of an intraoperative margin of revised bone 311A. Keyways 312A, 312B may be prepared in the manner described with respect to the dovetail groove shown and described in the '921 Patent. In process 200, an augmented cutting path that includes such keyways 312A, 312B is defined and an augmented cutting path data file is generated at step 225, as shown in FIG. 5. In arrangements preparing the one or more keyways 312A, 312B, spacer 395 is fabricated from a CAD model at step 170 when applying process 10 and at step 235 when applying process 200. Spacer 395 is the same or substantially the same as spacer 195 with the notable exception that spacer 395 includes protrusions 398A, 398B, which may be in the form of tongues when corresponding ones of the keyways are in the form of a groove such that the tongues together with the keyways form a "tongue-and-groove" joint as shown in FIG. 6. In this manner, protrusions 398A, 398B of spacer 395 may be slid into and along respective keyways 312A, 312B of revised bone 311A.

In some such arrangements, at step 175 during process 10 or step 275 during process 200, fabricated spacer 395 may be attached to revised bone 311A by way of insertion of protrusions 398A, 398B of the spacer within keyways 312A, 312B of the revised bone formed by the removal of bone structure using the augmented cutting path data file, and fabricated implant 55 may be attached to the spacer. In some arrangements, spacer 395 may be attached to implant 55, such as but not limited to by a fastener through both the spacer and the implant or by a later of bone cement between the spacer and the implant, prior to attaching the spacer, in combination with the implant, to revised bone 311A. In some other arrangements, spacer 395 may be attached to revised bone 311A prior to attaching implant 55 to the spacer which has been attached to the revised bone. Optionally, as in the example shown in FIG. 6, in still other arrangements, spacer 395 may be positioned with protrusions 398A, 398B within respective keyways 312A, 312B of revised bone 311A, and then implant 55 may be placed against the spacer and a fastener, such as a screw, may be inserted through hole 397 defined by each of the bone, the spacer, flange 57 and the implant to secure the bone, the spacer, and the implant together. In still further arrangements, implant 55 may act as a base onto which spacer 195 may be fabricated and to which the spacer may be fused using an additive manufacturing process.

Figure 7:
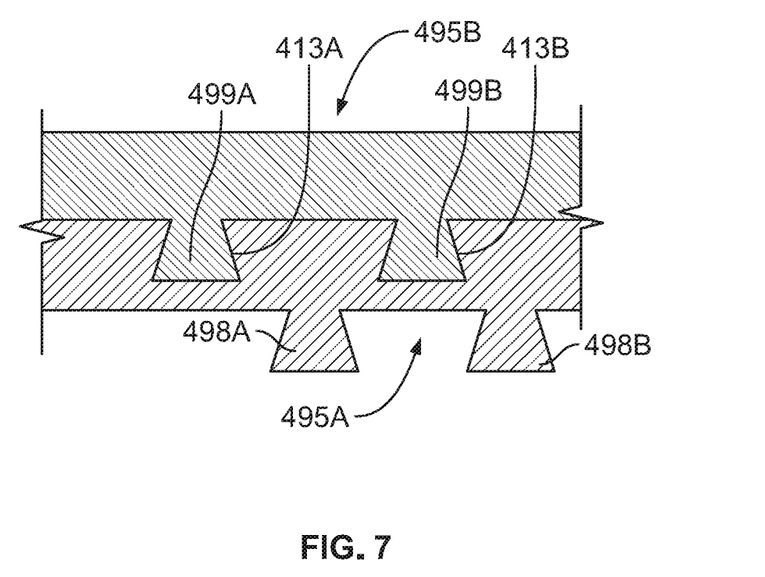
FIG. 7 is a cross-sectional view of a pair of interlocked spacers.

In some alternative arrangements, the fabricated spacer may be a plurality of fabricated spacers. In some arrangements, the plurality of fabricated spacers may be provided to a surgeon, via shipping to a medical facility or otherwise, at step 240 of process 200. As shown in the example of FIG. 7, spacers substantially in the form of fabricated spacer 395 may be stackable. In this example, spacer 495A is attachable to revised bone 311A in the same manner as spacer 395 by way of insertion of protrusions 498A, 498B of spacer 495A within corresponding bone keyways 312A, 312B of the revised bone. As further shown, spacer 495A includes spacer keyways 498A, 498B. An additional spacer 495B includes tongues 413A, 413B that may be inserted, such as by being slid, into and along spacer keyways 498A, 498B of spacer 495A to engage with spacer 495A as shown. Similar to the reversal of the keyways and tongues described previously herein, the tongues and keyways either one or both of the bone and spacer 495A interface and the spacer 495A and spacer 495B interface may be reversed.

In some alternative arrangements to the examples shown in FIGS. 6 and 7, the revised bone may include one or more tongues and the fabricated spacer may include the corresponding one or more keyways. In this manner, the spacer may be slid over and along the extending tongues of the revised bone.

In similar arrangements to the examples shown in FIGS. 6 and 7, any one or any combination of tongues 398A, 398B, 498A, 498B, 499A, 499B may be in the form of pegs, e.g., elongated pegs having circular, triangular, or rectangular cross-sections, and the keyways may be in the form of corresponding cavities for receiving such pegs. In some arrangements, the locations of the pegs and the cavities may be reversed such that the pegs and the cavities may be on other of the implant and bone parts relative to the arrangements shown in FIGS. 6 and 7.

Figure 8:
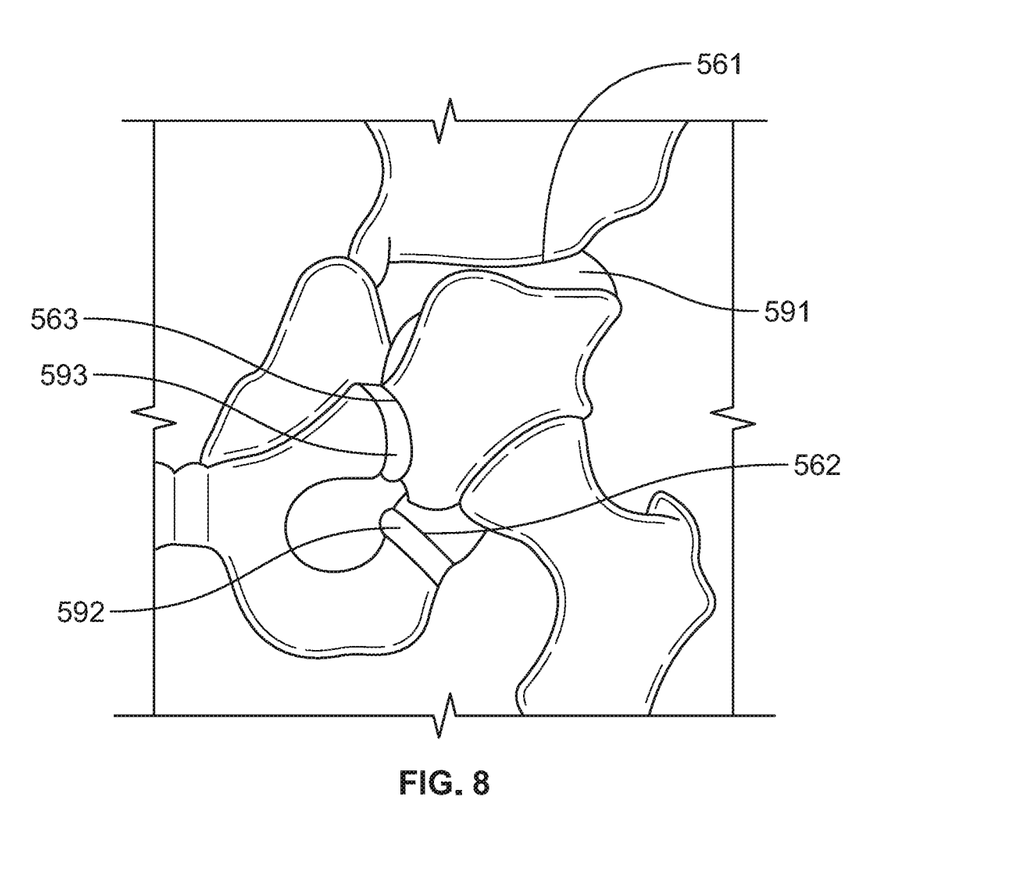
FIG. 8 is a perspective view of a patient's pelvic region following the insertion of spacers during a periacetabular (PAO) osteotomy surgery.

In one related arrangement, a plurality of preoperatively or intraoperatively fabricated spacers may be used for a periacetabular osteotomy (PAO) surgery to treat hip dysplasia whereby a patient's acetabulum is reoriented over a femoral head of the patient's femur. In an example shown in FIG. 8, such spacers are shims 591, 592, 593 inserted into three gaps formed by resections of a patient's pelvis at respective locations 561, 562, 563. The robot may be used to machine features into the bone to facilitate spacer placement and fixation. In some arrangements, the machined features may be keyways machined into the bone for receipt of corresponding tongues of the spacers for forming a tongue-and-groove joint as in the example of FIG. 6 described previously herein. The robot may be used to prepare, e.g., by drilling, holes in the acetabulum for use in fixating the spacers, in some arrangements in combination with the tongue-and-groove joint, to the acetabulum.

It is to be understood that the disclosure set forth herein includes any possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the technology, and in the technology generally.

Furthermore, although the technology herein has been described with reference to particular features, it is to be understood that these features are merely illustrative of the principles and applications of the present technology. It is therefore to be understood that numerous modifications, including changes in the sizes of the various features described herein, may be made to the illustrative embodiments and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A method of repairing a bone part, comprising the steps of:
attaching a patient-specific first implant to a first bone part, the first implant corresponding to an intraoperatively defined cutting path that is stored in a cutting path data file; and
attaching a preoperatively defined second implant to the first implant; and
at least partially fabricating the first implant intraoperatively from an implant data file prepared using the cutting path data file,
wherein the first implant and the second implant together augment the first bone part.

2. The method of claim 1, further comprising a step of attaching the second implant to a second bone part to form a joint defined by the first implant, the second implant, the first bone part, and the second bone part.

3. The method of claim 1, further comprising a step of resecting an initial bone part according to a preoperatively planned cutting path to form an intermediate bone part different from the first bone part, wherein the preoperatively planned cutting path differs from the intraoperatively defined cutting path.

4. The method of claim 1, wherein the second implant is an implant selected from the group consisting of a hip implant, a shoulder implant, a femoral implant, a tibial implant, a spine implant, a wrist implant, and a foot implant.

5. The method of claim 4, wherein the first implant is a shim.

6. The method of claim 1, wherein the second implant is configured to replace a mid-section of an initial bone part resected to form the first bone part.

7. The method of claim 1, wherein the second implant is a shim.

8. The method of claim 1, wherein the fabricating step includes three-dimensional (3D) printing of the first implant.

9. The method of claim 8, further comprising a step of generating a computer-aided design (CAD) model of the first implant intraoperatively for use in the 3D printing step.

10. The method of claim 9, further comprising a step of resecting an initial bone part to form the first bone part and to define a resected bone section, wherein the generating step includes generating a CAD model of the first implant via a step of performing a Boolean operation between a CAD model of the resected bone section and a CAD model of the second implant.

11. The method of claim 1, wherein the fabricating step includes either one or both of computer numerically controlled (CNC) milling or CNC lathing of a block of material.

12. The method of claim 1, wherein either one or both of the first implant and the second implant have a lattice structure, a unit cell structure, a woven structure, or a chain mail structure.

13. The method of claim 1, wherein the second implant is a patient-specific implant.

14. The method of claim 1, wherein the entirety of the first implant is fabricated intraoperatively.

15. The method of claim 1, wherein the first implant is fabricated by an additive manufacturing process.

16. The method of claim 1, wherein the first implant is fabricated by a computer-aided manufacturing process.

17. A method of repairing a bone part, comprising the steps of:
    resecting an initial bone part to form an intermediate bone part according to a preoperatively defined cutting path and to define a first resected bone section;
    resecting the intermediate bone part according to an intraoperatively selected cutting path to form a first bone part and to define a second resected bone section, the intraoperatively selected cutting path being selected among a plurality of preset cutting paths different from the preoperatively defined cutting path;
    attaching a first implant to the first bone part, the first implant corresponding to the intraoperatively selected cutting path; and
    attaching a preoperatively defined second implant to the first implant,
    wherein the second resected bone section corresponds to the first implant,
    wherein the first implant and the second implant together augment the first bone part, and
    wherein the intraoperatively selected cutting path is stored in a data file.

18. The method of claim 17, wherein the augmented first bone part has a predetermined structure corresponding to a CAD model.

19. The method of claim 17, wherein the preset cutting paths are preoperatively stored in respective data files.

* * * * *